United States Patent

Rosenthal et al.

[11] 3,931,324
[45] Jan. 6, 1976

[54] 2-HYDROCARBYL ETHERS OF CYCLOALIPHATIC KETONES AND PROCESS FOR THEIR PREPARATION

[75] Inventors: Rudolph Rosenthal, Broomall; Giovanni A. Bonetti, Ardmore, both of Pa.

[73] Assignee: Atlantic Richfield Company, Los Angeles, Calif.

[22] Filed: Nov. 20, 1973

[21] Appl. No.: 417,679

Related U.S. Application Data

[63] Continuation-in-part of Ser. No. 126,869, March 22, 1971, abandoned.

[52] U.S. Cl. ......... 260/586 R; 260/586 M; 260/590; 260/610 R; 260/613 R
[51] Int. Cl.² .......................................... C07C 45/00
[58] Field of Search ............ 260/586 R, 586 A, 590, 260/610 A, 613 R

[56] References Cited
UNITED STATES PATENTS

| | | | |
|---|---|---|---|
| 2,713,068 | 7/1955 | Spezale .......................... | 260/586 R |
| 3,431,308 | 3/1969 | Zimmermann et al...... | 260/586 R X |

Primary Examiner—Norman Morgenstern
Attorney, Agent, or Firm—John C. Martin, Jr.

[57] ABSTRACT

Compounds of the formula

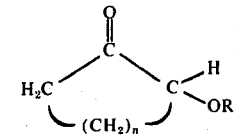

wherein R is a hydrocarbyl radical selected from the group consisting of alkyl, aralkyl and cycloalkyl having from 3 to 12 carbon atoms and n is an integer from 1 to 9 are prepared by reacting a 1,1-bis (hydrocarbyl peroxy) cycloalkane with cycloaliphatic ketones in the presence of a molybdenum containing catalyst. The 1,1-bis (hydrocarbyl peroxy) cycloalkane can be prepared in situ from an organic hydroperoxide and a cycloalkanone. The compounds have utility as solvents and certain specific members of the class have utility as intermediates to adipic acid by further oxidation or as an intermediate to 2-t-butoxyphenol by known dehydrogenation methods.

10 Claims, No Drawings

2-HYDROCARBYL ETHERS OF CYCLOALIPHATIC KETONES AND PROCESS FOR THEIR PREPARATION

RELATED APPLICATIONS

This application is a continuation-in-part of U.S. Pat. application Ser. No. 126,869, filed Mar. 22, 1971 now abandoned.

BACKGROUND OF THE INVENTION

1. Field of the Invention

This invention relates of 2-hydrocarbyl ethers of cycloaliphatic ketone compounds and methods for preparing said compounds.

2. Description of the Prior Art

U.S. patent application Ser. No. 16,564, filed Mar. 4, 1970, taught the reaction of an organic hydroperoxide and a ketone to produce diperoxide compounds of the formula

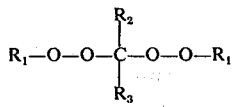

wherein $R_1$, $R_2$, and $R_3$ are independently selected saturated, substituted or unsubstituted organic radicals containing from 1 to 16 carbon atoms and wherein $R_2$ and $R_3$ can be joined in an alicyclic radical by the reaction of an organic hydroperoxide of the formula $R_1$—O—O—H and a ketone of the formula

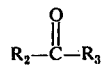

in the presence of molybdenum or vanadium.

SUMMARY OF THE INVENTION

We have discovered that 2-hydrocarbyloxy cycloalkanones can be prepared by reacting 1,1-bis (hydrocarbylperoxy) cycloalkanes with cycloalkanone in the presence of a molybdenum catalyst.

The 1,1-bis (hydrocarbylperoxy) cycloalkane can be produced in situ by the reaction of hydrocarbylhydroperoxide and cycloaliphatic ketones, the overall reaction being to react excess cycloaliphatic ketone with hydrocarbyl-hydroperoxide in the presence of a molybdenum catalyst to produce novel 2-hydrocarbyloxy cycloalkanones.

DETAILED DESCRIPTION OF THE INVENTION AND DESCRIPTION OF THE PREFERRED EMBODIMENTS

More particularly, the compounds of our invention have the structural formula

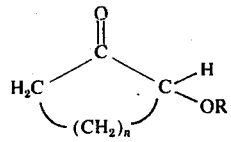

wherein R is a hydrocarbyl radical, preferably selected from the group consisting of alkyl, aralkyl, and cycloalkyl having from 3 to 12 carbon atoms, and n is an integer from 1 to 9. The 1,1-bis (hydrocarbylperoxy) cycloalkane starting materials are known compounds and are produced by prior art methods or by reacting two moles of a hydrocarbyl hydroperoxide with one mole of cycloalkanone in the presence of molybdenum as shown in U.S. Ser. No. 16,564, supra.

Alternatively, the 1,1-bis (hydrocarbylperoxy) cycloalkane may be produced in situ by reacting hydrocarbyl hydroperoxide with excess cycloalkanone in the presence of molybdenum catalyst producing the 1,1-bis (hydrocarbylperoxy) cycloalkane which reacts in the same reaction medium with the excess cycloalkanone to form the novel compounds of this invention.

Suitable cycloalkanones are those having from 4 to 12 carbon atoms and are preferably unsubstituted, for example, cyclobutanone, cyclopentanone, cyclohexanone, cycloheptanone, cyclooctanone, cyclononanone, cyclodecanone, cycloundecanone, and cyclododecanone.

Suitable hydrocarbyl hydroperoxides are those having from 3 to 12 carbon atoms and preferably alkylhydroperoxide, cycloalkylhydroperoxide or aralkylhydroperoxide. Exemplary hydroperoxides are isopropylhydroperoxide, t-butylhydroperoxide, t-amylhydroperoxide, cumene hydroperoxide, cyclohexylhydroperoxide, tetralylhydroperoxide, and ethylbenzene hydroperoxide. The molar ratio of cycloalkanone to 1,1-bis (hydrocarbylperoxy) cycloalkane is from about 1:1 to about 10:1. When the 1,1-bis (hydrocarbylperoxy) cycloalkane is produced in situ it is required that there be an excess of cycloalkanone to drive the reaction to completion.

The reactant may be combined in any order of addition and reaction times are from a few minutes to a few hours depending upon temperature and other reaction conditions. The 2-hydrocarbyloxy cycloalkanone products may be recovered by any conventional method, for example, by distillation of the reaction product under reduced pressure. Among the products produced according to this invention are 2-isopropoxycyclohexanone, 2-t-butoxycyclobutanone, 2-t-butoxycyclopentanone, 2-t-butoxycyclohexanone, 2-t-butoxycycloheptanone, 2-t-butoxycyclooctanone, 2-t-butoxycyclononanone, 2-t-butoxycyclodecanone, 2-t-butoxycycloundecanone, 2-t-butoxycyclododecanone; the 2-t-amyl ethers of cyclobutanone, cyclopentanone, cyclohexanone, cycloheptanone, cyclooctanone, cyclononanone, cyclodecanone, cycloundecanone, and cyclododecanone; the 2-cumyl ethers of cyclobutanone through cyclododecanone; the 2-cyclohexyl ether of cyclobutanone through cyclododecanone; the 2-tetralylether of cyclobutanone through cyclododecanone; and the 2-ethylbenzene ethers of cyclobutanone through cyclododecanone.

Any suitable source of molybdenum catalyst can be used. Molybdenum is preferably present in a range of from about 100 ppm to about 1 wt. % of the reaction mixture and most preferably from 300 to 5,000 ppm. Both metallic molybdenum and compounds of molybdenum may be used. Molybdenum compounds include the oxides, for example, molybdenum dioxide, molybdenum sesquioxide, molybdenum trioxide, molybdenum pentoxide, the chlorides and oxychlorides, for example, molybdenum pentachloride, molybdenum fluoride, and in particular the acids and the corresponding salts wherein the molybdenum is contained in the anionic portion of the molecule. Molybdic acid, and its corresponding salts, the molybdates, are particularly useful as catalyst components. In addition to these simple compounds the high molecular weight complex heteropoly acids and salts are particularly useful and combinations of the simple salts with the heteropoly salts have been found useful. Illustrative soluble forms of the catalytic materials are the naphthenates, stearates, octoates, carbonyls and the like. Various chelates and enol salts, such, for examples, as acetylacetonates may also be used. Specific and preferred catalytic compounds of this type for use in the invention are molybdenum naphthenates and molybdenum carbonyls such as molybdenum hexacarbonyl.

The use of inert solvents is optional in the process of this invention.

The following examples are presented to illustrate the process of the invention but are not to be construed as limiting.

EXAMPLE I

A mixture of 50 grams of cyclohexanone, 10 grams t-butylhydroperoxide, and 0.5 gram of a molybdenum naphthenate solution containing 5 wt. % molybdenum was stirred at room temperature for one hour. Titration indicated that 54% of the t-butylhydroperoxide had reacted at this point and glpc analysis indicated that 1,1-bis (t-butylperoxy) cyclohexane was formed. An additional 0.5 grams of 5 wt. % molybdenum naphthenate and 2 grams of cyclohexanone was added and stirring was continued for an additional hour and thereafter heated to 80° to 85°C. for three hours. The 1,1-bis (t-butylperoxy) cyclohexane was almost completely converted to 2-t-butoxycyclohexanone.

EXAMPLE II

In a like manner, other hydrocarbyl hydroperoxides may be substituted for t-butylhydroperoxide and other cycloalkanones may be substituted for cyclohexanone to produce the desired 2-hydrocarbyloxy cycloalkanone.

The 2-hydrocarbyloxy cycloalkanones prepared according to the invention may be used as solvents and certain members of the class may be converted to adipic acid by further oxidation. Furthermore, 2-t-butoxyphenol may be prepared by catalytic dehydrogenation (known methods) of 2-t-butoxycyclohexanone. Thereafter, 2-t-butoxyphenol may be condensed with formaldehyde to form nuclear-substituted phenol-aldehyde resins useful as adhesives. In addition, 2-hydrocarbyloxy cycloalkanones may be used a organic solvents in insecticide formulations, particularly for organic insecticides; for instance, any of the 2-hydrocarbyloxy cycloalkanones may be used as a solvent for dichloro-diphenyl-trichloromethane (DDT). 2-isopropoxycyclohexanone is useful as an intermediate for making pesticides wherein it is catalytically dehydrogenated to 2-isopropoxyphenol and reacted with methyl isocyanate to yield 2-isopropoxyphenyl-N-methylcarbamate. Specific preparative steps are described in U.S. Pat. No. 3,111,539 and Netherlands Patent Publication 71-17520.

While the invention has been described in considerable detail, it will be appreciated by those skilled in the art that various modifications and alterations may be made without departing from the spirit and the scope of the invention.

We claim:

1. A process for preparing 2-hydrocarbyloxy cycloalkanones comprising reacting a 1,1-bis (hydrocarbylperoxy) cycloalkane with cycloalkanone in the presence of a molybdenum containing catalyst selected from the group consisting of metallic molybdenum and compounds of molybdenum at a reaction temperature of from about 20°C. to about 150°C.; the molar ratio of cycloalkanone to 1,1-bis (hydrocarbylperoxy) cycloalkane being from about 1:1 to about 10:1.

2. The process of claim 1 wherein the catalyst is present in a range of from about 0.01 wt. % to 2 wt. % of the total weight of the starting materials.

3. The process of claim 2 wherein the catalyst is molybdenum naphthenate.

4. The process of claim 2 wherein pressures are from about atmospheric to about 100 atmospheres.

5. The process of claim 1 whrein said cycloalkanone is cyclohexanone.

6. A process for preparing 2-t-butoxycyclohexanone comprising reacting at a temperature of from about 20°C. to about 150°C. (a) cyclohexanone with (b) 1,1-bis (t-butylperoxy) cyclohexane in the presence of a molybdenum containing catalyst wherein the molar ratio of (a) to (b) is from about 1:1 to about 10:1.

7. The process of claim 6 wherein said catalyst is molybdenum naphthenate.

8. The process of claim 6 wherein the reaction is carried out in the presence of an inert solvent.

9. A process for preparing 2-isopropoxycyclohexanone comprising reacting at a temperature of from about 20°C. to about 150°C. (a) cyclohexanone with (b) 1,1-bis (isopropylperoxy) cyclohexane in the presence of a molybdenum containing catalyst wherein the molar ratio of (a) to (b) is from about 1:1 to about 10:1.

10. The process of claim 1 wherein said compound of molybdenum is selected from the group consisting of molybdenum oxides, molybdenum chlorides, molybdenum fluoride, molybdic acid, molybdic acid salts, molybdenum naphthenates, molybdenum stearates, molybdenum octoates, molybdenum carbonyls, and molybdenum acetylacetonates.

* * * * *